United States Patent [19]
Lindenberg et al.

[11] Patent Number: 5,716,393
[45] Date of Patent: Feb. 10, 1998

[54] STENT WITH AN END OF GREATER DIAMETER THAN ITS MAIN BODY

[75] Inventors: Josef Lindenberg, Pörtschach, Austria; Wolfram Schnepp-Pesch, Karlsruhe, Germany

[73] Assignee: Angiomed GmbH & Co. Medizintechnik KG, Karlsruhe, Germany

[21] Appl. No.: 586,696

[22] PCT Filed: May 20, 1995

[86] PCT No.: PCT/EP95/01925

§ 371 Date: Feb. 26, 1996

§ 102(e) Date: Feb. 26, 1996

[87] PCT Pub. No.: WO95/32688

PCT Pub. Date: Dec. 7, 1995

[30] Foreign Application Priority Data

May 26, 1994 [DE] Germany .................. 44 18 336.4

[51] Int. Cl.$^6$ ............................................. A61F 2/06
[52] U.S. Cl. ............................................. 623/1
[58] Field of Search ........................... 623/1, 11, 12; 606/191, 194, 195, 198

[56] References Cited

U.S. PATENT DOCUMENTS

| | | |
|---|---|---|
| 4,494,066 | 1/1985 | Voss . |
| 5,064,435 | 11/1991 | Porter .................................. 623/12 |
| 5,330,500 | 7/1994 | Song .................................... 623/1 |
| 5,354,309 | 10/1994 | Schnepp-Pesch et al. ............. 623/1 |
| 5,382,261 | 1/1995 | Palmaz ................................ 623/12 |
| 5,395,390 | 3/1995 | Simon et al. ......................... 623/1 |

FOREIGN PATENT DOCUMENTS

| | | | |
|---|---|---|---|
| 2189150 | 10/1987 | United Kingdom . | |
| 9317636 | 7/1993 | WIPO .................... | 623/1 |
| 9417754 | 8/1994 | WIPO .................... | 623/1 |

*Primary Examiner*—Michael J. Milano
*Assistant Examiner*—Tram Anh T. Nguyen
*Attorney, Agent, or Firm*—Antonelli, Terry, Stout, & Kraus, LLP

[57] ABSTRACT

For the better anchoring of a stent in its use area within a vessel, in the case of a stent expandable from a radially contracted introduction state into a radially expanded position state, in the radially expanded state at least one front end of the stent has a greater diameter than the remaining main stent body with ribs of the front end being longer than those in the main stent body.

12 Claims, 3 Drawing Sheets

5,716,393

STENT WITH AN END OF GREATER DIAMETER THAN ITS MAIN BODY

FIELD OF INVENTION

The invention relates to a stent for dilating and keeping open vessels, with a radially contracted state for introduction into the vessel and with a radially expanded state after introduction into the vessel.

BACKGROUND AND SUMMARY OF INVENTION

Such stents or implantable catheters to be introduced into a body cavity, a vessel or the like can be made from plastic or an inert metal, such as steel or nickel-titanium alloys. Such stents are also referred to as endovascular or endoluminal stents or endoprostheses. For example when dilating the ureter the stents are used in the prostate region in the case of benign prostate hyperplasia (BPH) or also in sclerotic blood vessels for dilating and keeping open the same. The stents have material areas and gaps between them. Thus, it is possible for the wall tissue of the organ kept open to grow round the stent. Stents can have a spiral construction or can be in the form of a helically wound coil. They can be made from woven or knitted wire or plastic material. Such stents can have memory properties, such as e.g. exist with certain nickel-titanium alloys (nitinol).

The problem of the invention is to ensure a secure anchoring of such a stent in the vessel to be dilated.

According to the invention the set problem is solved in the case of such a stent in that in the radially expanded state at least one front end has a greater radial extension than the remaining main body of the stent.

In the case of a scent, which is formed by ribs and free spaces left between the same, according to a preferred development of the invention in the vicinity of at least one front end of the stent the ribs have a greater length than corresponding ribs of the main stent body and in particular the length of the ribs in the front region can be 120 to 190% of the length of the ribs in the main stent region.

According to further preferred developments of the invention, in the front side areas the ribs extend radially further outwards than the ribs in the main stent area and the ribs in the front side area form a finite angle to the major axis of the stent.

The free spaces can either be diamond-shaped or honeycombed. The stent is preferably self-expanding and in a preferred development not solely due to elastic properties and introduction in a state under radial tension, but as a result of the fact that it is made from a memory metal.

In order to attain a greater bendability and flexibility of the stent, according to a further preferred development, between axially succeeding ribs are provided in part gaps and in part connecting areas. This is achieved by a higher flexibility than would be the case with a stent in which axially succeeding ribs were firmly interconnected in the connecting areas. There is also no cross-sectional deformation when bending under the action of vertical axial forces.

Due to the fact than the stent is constructed in single layer form, a high bendability is obtained without metal crossing points, such as is the case with knitted and braided structures and the like, which give rise to a greater material thickness. There can be a better growing in of the stent into the tissue. The risk of thromboses occurring, particularly in the vascular area is significantly reduced or virtually excluded.

In a preferred development, the connecting areas are circumferentially mutually displaced. This leads to the retention or obtaining of the desired axial strength (i.e. against compression and tension in the axial direction) in the case of bending resistance perpendicular to the axis.

According to further preferred developments the stent is made from a flat plate from which are cut slots for forming the gaps, the flat plates being connected together, particularly by welding, in the marginal areas after bending to a cylindrical contour and the free spaces are formed by slots after heat treatment.

Further advantages and features of the invention can be gathered from the claims and description of a preferred embodiment of the invention with reference to the drawings.

DETAILED DESCRIPTION OF DISCLOSED EMBODIMENT

Figure 1:
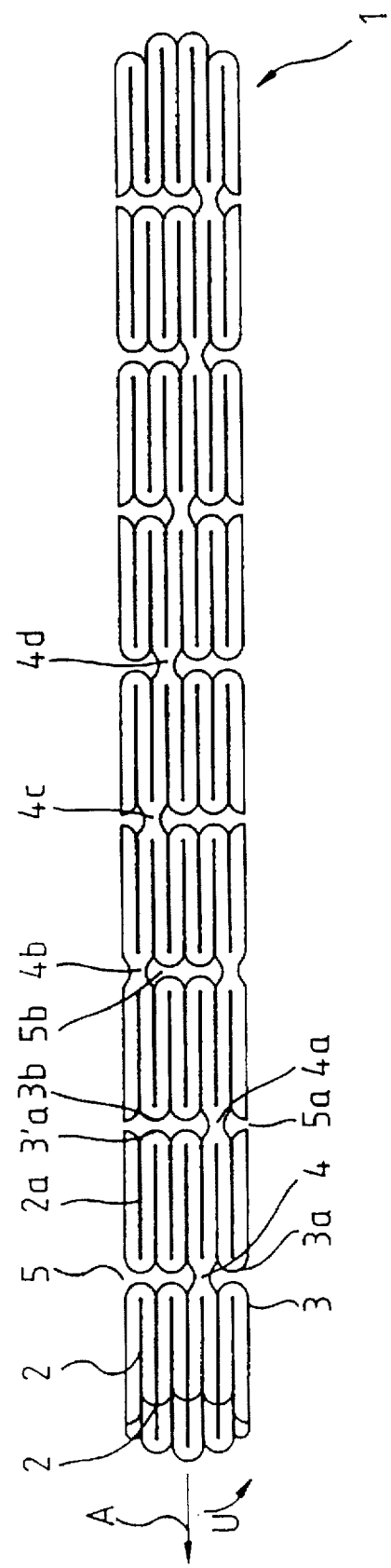
FIG. 1 is a preferred development of the stent according to the invention in its radially contracted low temperature or introduction state.

In its radially contracted state for introduction into the vessel to be dilated, the stent 1 according to the invention has a cylindrical shape or an outer contour as shown in FIG. 1. In the expanded state the stent 1 according to the invention has over the length L of its main body, i.e. its greatest length, a cylindrical outer contour. However, in the vicinity of its two front ends 1b, 1c, the stent according to the invention is radially expanded over the radial dimensions, i.e. the diameter D of the main body 1a, so that the stent 1 can be anchored with its radially expanded ends 1b, 1c on the vessel wall.

Figure 2:
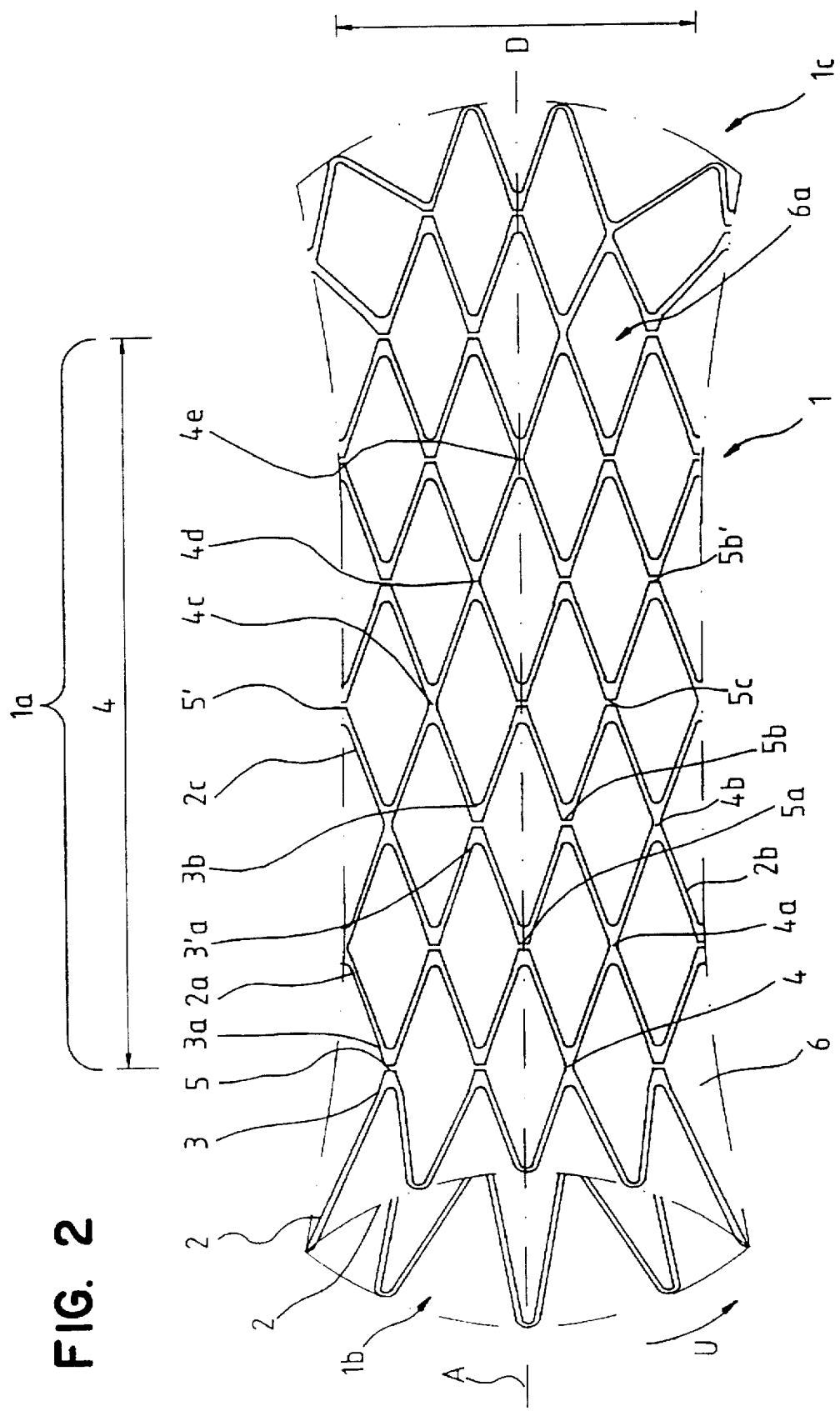
FIG. 2 shows the stent according to the invention in its radially expanded high temperature or use state.

As is in particular made clear by FIG. 2, the stent 1 according to the invention is formed from a plurality of meander paths arranged successively over the circumference of the stent 1 in the form of angularly interconnected ribs 2 or 2a or 2b in the connecting or tip regions 3, 3a, 3'a, 3b. In the circumferential direction the meander paths or ribs 2, 2a, 2b are so arranged that in each case facing, adjacent connecting or tip regions 3, 3a or 3'a, 3b of juxtaposed meander paths or ribs 2, 2a, 2b are axially aligned.

FIG. 2 also clearly shows than the axially succeeding meander paths formed by the ribs 2, 2a, 2b in the vicinity of their tip or connecting regions 3, 3a, 3'a, 3b are not interconnected by transitions 4, 4a, 4b, 4c, 4d, 4e but in the circumferential direction between such transitions 4 to 4d of two adjacent meander paths formed by the ribs 2, 2a are located several gaps 5, 5', 5a, 5b, 5b', 5c etc. The transition areas 4 to 4d and gaps 5 to 5b' are jointly also referred to as nodal areas.

Considered in another way, the stent according to the invention can be so formed by ribs 2, 2a, 2b and free spaces 6, 6a formed between thereto the free spaces 6, 6a in the embodiment shown having the contour of a diamond, i.e. are bounded by four rib areas, but could also be shaped like a honeycomb, that being bounded by six rib areas. The nodal areas in this case are partly left as connections 4 to 4d, whereas in other areas they are split by the gaps 5 to 5b'. The connections or transitions 4 to 4d are not axially aligned, but are in each case angularly or circumferentially displaced.

The gaps 5 to 5b', etc. lead to a high flexibility of the stent according to the invention. It is in particular attained that the stent 1, on bending perpendicular to its longitudinal axis A and therefore bending of the longitudinal axis itself does not kink or bend in in the central area in such a way that it loses its cross-sectionally substantially circular contour and in the action direction of the forces is centrally pressed flat and perpendicular the action direction of the forces is widened roughly in the centre of its longitudinal extension, as occurs with conventional stents, where all the facing, adjacent tip or connecting areas 3, 3a, etc. in axially juxtaposed meander turns are firmly connected by connecting areas or transitions 4, 4a. The connecting areas or transitions 4, 4a, etc. are constructed in one piece with the remaining parts of the stent, particularly the ribs 2, 2a, etc. and their adjacent tip or connecting areas 3, 3a.

FIG. 1 shows that the substantially diamond-shaped free spaces (FIG. 2) formed between the ribs 2, 2a, etc. of the meander paths in the high temperature position taper to slots in the low temperature or introduction position and the ribs 2, etc. of the meander paths are substantially parallel to one another.

Figure 3:
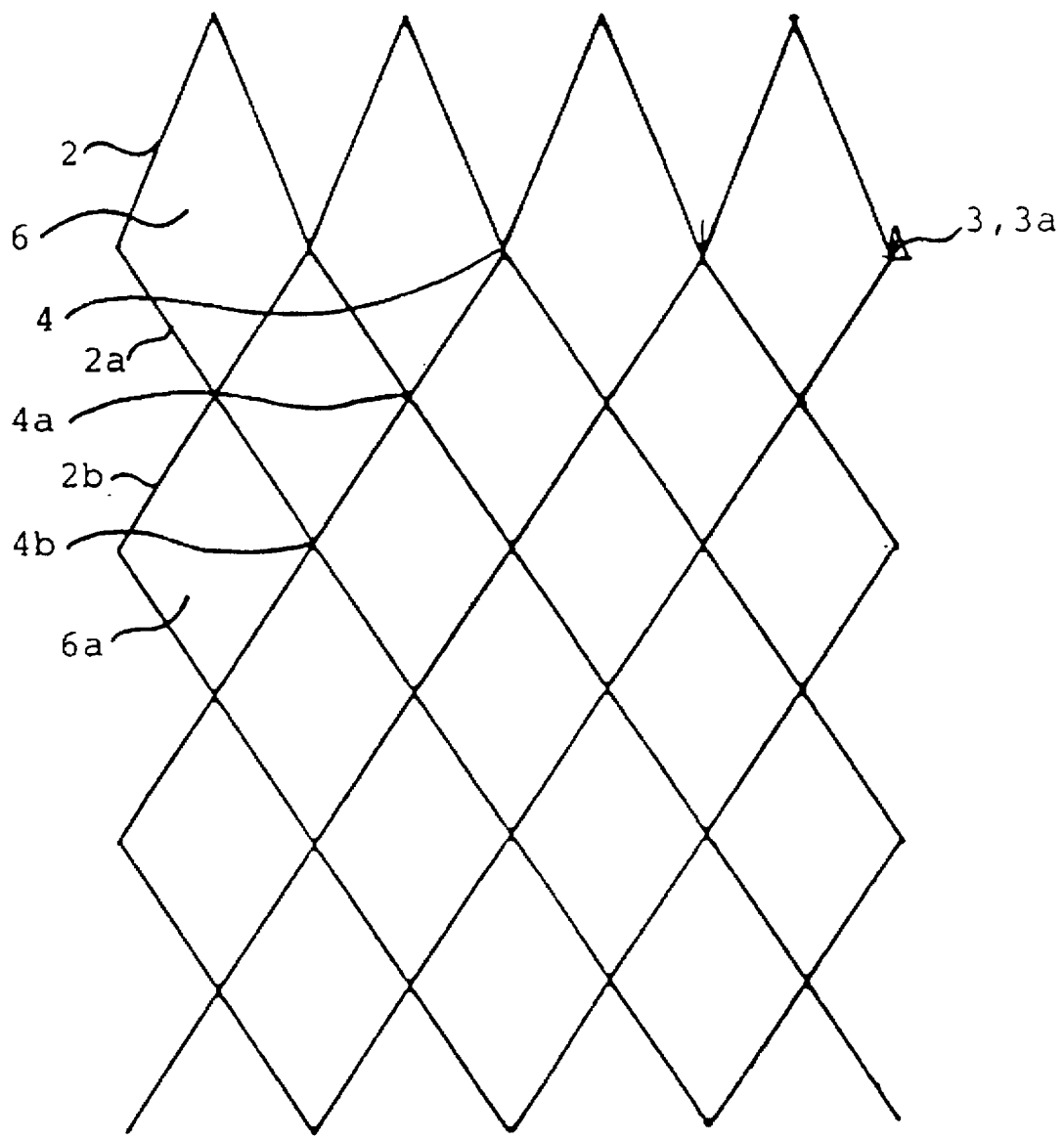
FIG. 3 A highly diagrammatic representation of part of a stand for illustrating the design on the front ends.

FIG. 3 more particularly shows that the length of the ribs 2 of the outer or frontal meander areas is much greater than the ribs 2a, 2b in the main body 1a of the stent 1 according to the invention. The length of the end ribs 2 can be between 120 and 200% of the ribs 2a to 2c of the main body. The length ratio can largely be chosen at random and is determined by the permitted expansion, the necessary stent length and the desired radial dilation of the end regions 1b, 1c over the main body 1a of the stent 1.

The stent 1 according to the invention is made from a nickel-titanium alloy, such as nitinol. It is produced in such a way that the metal plate or sheet is initially very accurately etched to the desired thickness, namely with a tolerance range of 0.001 mm. The parts forming the stent are then cut from a large-area plate. Said plate parts are then cut to form the openings or slots in such a way that circumferentially adjacent slots are axially displaced by half their length. The cutting of the slots takes place by means of a laser. In the central area of each slot the latter is provided with an expansion, so that the material binding the latter in the circumferential direction is reduced roughly to the width of the material remaining between the slots. These portions, if left standing, subsequently form the connecting portions 4, 4a, or the free spaces or gaps 5, 5a, etc. are created in their areas if the portions are removed. After cutting the slots the cutout parts are broken off and the slotted plate is deburred. The slotted plate is then bent to a cylinder, so that the lateral edges are in contact. Welds are then made on tongues or flaps, so that the stent is obtained in its low temperature position according to FIG. 1. This is followed by a heat treatment, in order to give the stent memory properties, so that after raising the temperature above a predetermined ambient temperature, which is well below the temperature of the human body, it can dilate to its high temperature position according to FIG. 2 which it reaches at a maximum temperature of 35° C.

After producing and heat treating the stent in this way, the bridges are removed in the desired manner, so that the connecting areas or webs 4, 4a or free spaces 5, 5', 5a, etc. are formed, as described hereinbefore. This is followed by grinding and polishing, preferably in a rotary drum machine. The stents are then checked for dimensions, function and setting. This is followed by cleaning in an ultrasonic bath, initially with a soap solution, then with distilled water and finally with alcohol.

We claim:

1. Stent for dilating and keeping open a vessel, said stent comprising a body with means for permitting the stent to be radially contracted to a radially contracted state for introduction into the vessel and to be radially expanded to a radially expanded state after introduction into the vessel, and wherein said stent in the radially expanded state having at least one front end which has a greater diameter than the remaining body of the stent between its ends, wherein said body has ribs and free spaces between said ribs, and wherein ribs of said at least one front end of the stent have a greater length than the ribs of the remaining body of the stent between its ends.

2. Stent according to claim 1, wherein the length of the ribs in said front-end is 120 to 190% of the length of the ribs in said remaining body of the stent.

3. Stent according to claim 1 wherein said front end ribs extend further radially outward than the ribs in said remaining body of the stent.

4. Stent according to claim 1, wherein the ribs in said front end form a finite angle with a major axis of the stent.

5. Stent according to claim 1 wherein said free spaces are diamond-shaped.

6. Stent according to claim 1, wherein said stent is self-expanding.

7. Stent according to claim 1, wherein said stent is made from a memory metal.

8. Stent according to claim 1, wherein said ribs of said stent form a plurality of meander paths arranged successively in the axial direction of said stent and spanning its circumference, and wherein between axially succeeding ribs of axially adjacent meander paths there are gaps and connecting areas.

9. Stent according to claim 8, wherein the connecting areas are circumferentially displaced from one another with said gaps intervening.

10. Stent according to claim 1, wherein said stent body is made from a flat plate from which slots are cut for forming gaps as said free spaces, the said flat plate having lateral edges which are connected together, following bending of said flat plate to a cylindrical contour.

11. Stent according claim 1, wherein said free spaces are formed by slots in said body after heat treatment.

12. Stent according to claim 1, wherein said stent is constructed in single layer form.

* * * * *